United States Patent
Brunner et al.

(10) Patent No.: US 8,529,937 B2
(45) Date of Patent: Sep. 10, 2013

(54) UHMWPE MEDICAL IMPLANT PRODUCING WEAR PARTICLES WITH BENIGN BODY RESPONSE

(75) Inventors: Lorenz Brunner, Zurich (CH); Yvo Dirix, Erlenbach (CH); Shilesh C. Jani, Memphis, TN (US); Roberto Tommasini, Uster (CH)

(73) Assignee: Smith & Nephew Orthopedics AG, Rotkreuz (CH)

( * ) Notice: Subject to any disclaimer, the term of this patent is extended or adjusted under 35 U.S.C. 154(b) by 0 days.

(21) Appl. No.: 13/202,396

(22) PCT Filed: Feb. 19, 2009

(86) PCT No.: PCT/US2009/034568
§ 371 (c)(1),
(2), (4) Date: Feb. 10, 2012

(87) PCT Pub. No.: WO2010/096053
PCT Pub. Date: Aug. 26, 2010

(65) Prior Publication Data
US 2012/0129948 A1    May 24, 2012

(51) Int. Cl.
*A61F 2/02* (2006.01)
(52) U.S. Cl.
USPC ........................................................ 424/425
(58) Field of Classification Search
None
See application file for complete search history.

(56) References Cited

U.S. PATENT DOCUMENTS

| 6,277,390 | B1 | 8/2001 | Schaffner |
| 2007/0059334 | A1 | 3/2007 | Abt et al. |
| 2009/0030524 | A1 | 1/2009 | Schroeder et al. |

FOREIGN PATENT DOCUMENTS

| CN | 1618473 | 5/2005 |
| EP | 1 779 877 A1 | 5/2007 |
| WO | WO 00/64505 | 11/2000 |
| WO | WO 2007/056667 A2 | 5/2007 |
| WO | WO 2008/006890 A2 | 1/2008 |
| WO | WO 2008/101134 A1 | 8/2008 |
| WO | WO 2008/113388 A1 | 9/2008 |

OTHER PUBLICATIONS

European Examination Report; European Application No. 09 789 470.3; Oct. 30, 2012; 4 pages.
C.J. Grobbelaar et al., The Radiation Improvement of Polyethylene Prosthesis A Preliminary Study, The Journal of Bone and Joint Surgery, Aug. 1978, pp. 370-374, vol. 60-B, No. 3.
Hans-Georg Willert, M.D. et al., Osteolysis in Alloarthroplasty of the Hip, Department of Orthopaedics, University of Gottingen, Clinical Orthopaedics and Related Research, Sep. 28, 1989, pp. 95-107.
Hironobu Oonishi et al., Gamma-Irradiated Cross-Linked Polyethylene in Total Hip Replacements—Analysis of Retrieved Sockets After Long-Term Implantation, pp. 167-171, Copyright 2001 John Wiley & Sons, Inc.
Radha K. Maheshwari et al., Multiple Biological Activities of Curcumin: A Short Review, Life Sciences 78, 2006, pp. 2081-2087, Published by Elsevier Inc.

(Continued)

*Primary Examiner* — Carlos Azpuru
(74) *Attorney, Agent, or Firm* — Krieg DeVault LLP

(57) ABSTRACT

A substance, which contains anti-inflammatory substances, anti-microbial substances, anti-tumor substances, anti-viral substances, and/or bone stimulating substances, as an additive, can be added to an UHMWPE material for the production of a medical implant for imparting benign body response properties to the medical implant.

29 Claims, 2 Drawing Sheets

(56) References Cited

OTHER PUBLICATIONS

James A. D'Antonio, MD et al., Five-Year Experience with Crossfire Highly Cross-Linked Polyethylene, Clinical Orthopaedics and Related Research, Dec. 2005, pp. 143-150, No. 441, Copyright 2005 Lippincott Williams & Wilkins.

Georgios Digas, MD et al., Highly Cross-Linked Polyethylene in Cemented THA, Clinical Orthopaedics and Related Research, Dec. 2003, pp. 126-138, No. 417, Copyright 2003 Lippincott Williams & Wilkins, Inc.

Steven M. Kurtz, PhD et al., Degradation of Mechanical Properties of UHMWPE Acetabular Liners Following Long-Term Implantation, The Journal of Arthroplasty, Oct. 1, 2003, pp. 68-78, vol. 18 No. 7, Copyright 2003 Elsevier Inc.

C. Anderson Engh Jr., MD et al., A Randomized Prospective Evaluation of Outcomes After Total Hip Arthroplasty Using Cross-Linked Marathon and Non-Cross-Linked Enduron Polyethylene Liners, The Journal of Arthroplasty, Sep. 2, 2006, pp. 17-25, vol. 21. No. 6, Copyright 2006 Elsevier Inc.

L. Costa et al., Oxidation of Orthopaedic UHMWPE, Biomaterials 23, 2002, pp. 1613-1624, Copyright 2002 Elsevier Science Ltd.

European Examination Report; European Application No. 09 789 470.3; May 23, 2013; 4 pages.

UHMWPE MEDICAL IMPLANT PRODUCING WEAR PARTICLES WITH BENIGN BODY RESPONSE

BACKGROUND OF THE INVENTION

1. Field of the Invention

The invention relates generally to medical implants, especially medical implants eliciting a benign body response.

2. Description of the Related Art

Ultra-high molecular weight polyethylene ("UHMWPE") is the most commonly used bearing material in total joint replacements and was introduced by John Charnley in the early 1960s (The UHMWPE Handbook, edited S. Kurtz, Elsevier, 2004). Since then, a wide variety of applications have been developed in the total joint arthroplasty, as a result of the material's high toughness and good mechanical properties. UHMWPE is one of the only polymers that is used in its pure form and does not contain additives (ASTM F 648-07).

Although "conventional" UHMWPE has an excellent clinical record, the maximum lifetime of implant systems is restricted due to the wear particles released from the UHMWPE bearing surface (Willert H. G., Bertram H., Buchhorn G. H., Clin Orthop 258, 95, 1990). The negative biological effects of wear particles are considered to be the most important limiting factors for a long implant life. The liberation of sub micron size wear debris into human tissue leads to chronic inflammation. Continuous inflammation caused by UHMWPE particles activates inflammatory cells (macrophages) that stimulate bone resorptive cells (osteoclasts) and eventually a loosening of the implant.

In the 1970s, highly crosslinked UHMWPEs have been introduced with the intention of improving the wear resistance of the material (Oonishi H., Kadoya Y., Masuda S., Journal of Biomedical Materials Research, 58, 167, 2001; Grobbelaar C. J., du Plessis T. A., Marais F., The Journal of Bone and Joint Surgery, 60-B, 370, 1978). The UHMWPE materials were gamma irradiated at high doses up to 100 Mrad, this is in contrast to gamma sterilized UHMWPE which typically receive a dose ranging between 2.5 and 4.0 Mrad. The high doses were used to promote the crosslinking process in the material and thereby increase the wear resistance. Hence, the crosslinking process led to a reduction of the wear particles and therefore also to a reduction of malign body response reactions. A disadvantage of the highly crosslinked materials was that there were still free radicals present in the material, potentially leading to oxidative degradation.

The energy of the gamma rays is sufficient to break some of the carbon-carbon or carbon-hydrogen bonds of the polyethylene chains resulting in the formation of free radicals. These radicals partially recombine but some of them are long-living and can react with oxygen present in, or diffusing into, the packaging surrounding the implant (Costa L., Jacobson K., Bracco P., Brach del Prever. E. M., Biomaterials 23, 1613, 2002). The oxidative degradation reactions lead to embrittlement of the material and therewith reduce the mechanical properties of the material and might lead to fracture of the implant (Kurtz S. M., Hozack W., Marcolongo M., Turner J., Rimnac C., Edidin A., J Arthroplasty 18, 68-78, 2003).

Quenching of free radicals by heat treatment either above or below the crystalline melt temperature of UHMWPE has been known for a long time (S. Kurtz, The UHMWPE Handbook, Elsevier Academic Press, 2004, p. 112). Hence, in the 1990's, highly crosslinked materials were developed that were thermally treated (annealed or remelted) after the irradiation process to combine enhanced wear with oxidative stability since the residual free radicals were quenched during the thermal treatment process.

Despite the lower wear rate, and therefore lower volume of wear particles, of highly crosslinked UHMWPE, which was confirmed by clinical studies, the osteolysis did not disappear completely. In several studies, osteolytic regions or radiolucent zones were described for implant systems using highly crosslinked UHMWPE (J. A. D'Antonio et al., Clinical Orthopaedics and Related Research, 441, 2005; C. A. Engh et al., The Journal of Arthroplasty, 21 (6 Suppl. 2), 2006; G. Digas et al., Clinical Orthopaedics and Related Research, 417, 2003). Hence, even the low amount of wear particles generated by highly crosslinked UHMWPE is able to start an inflammatory reaction which finally leads to osteolysis.

Curcumin, a component of the Indian spice turmeric, is well documented for its medicinal properties in Indian medicine. Apart from other beneficial properties, curcumin is described to have anti-oxidant and anti-inflammatory properties (R. K. Maheshwari et al., Life Sciences, 78 (18), 2006; A. Sahu, Acta Biomaterialia, Article in Press, 2008; S. Merell et al., Presentation at the World Biomaterials Conference, Amsterdam 2008; The University of Texas MD Anderson Cancer Center, Webpage: http://www.mdanderson.org/departments/cimer/).

Other literature studies describe beneficial properties of different substances: In a very recent study, quercetin was described to promote bone formation when mixed into collagen matrix (R. W. K. Wong et al., Journal of Orthopaedic Research, 26 (8), 2008). Another study describes a reduced osteolysis induced by tumor extracts by the addition of diphosphonates (A. Jung et al., Schweiz. Med. Wochenschr., 109 (47), 1979. The same effect of diphosphonates was shown in another study (C. S. B. Galasko et al., Paper presented at the Fourth Tripartite Surgical Meeting, Oxford, England, 5-7 Jul. 1979).

SUMMARY OF THE INVENTION

Given the above-mentioned problems relating to UHMWPE materials used for medical implants, it is an objective of the present invention to provide an improved UHMWPE material that allows the formation of medical implants which overcome the negative biological effects associated with previously known medical implant materials.

The goal of the present invention is to provide a material for use in medical implants, in particular in the form of artificial joint replacements, which produces wear particles which exhibit benign body response properties. Up to date, wear particles generated from artificial joint replacements were often related to inflammation, osteolysis or other negative body responses. In one embodiment of the present invention, a material is described which is blended with a natural additive that exhibits benign body response properties, e.g. anti-inflammatory, anti-tumor, anti-microbial or the such.

Accordingly, the teaching of the present invention marks a turning point in the strategy to improve the long-time biological effects of medical implants. Previous approaches to improve the long-time biological effects of medical implants have focussed on improving the wear resistance of the material of the medical implants in order to minimize the production of wear particles related to inflammation, osteolysis and other negative body responses. In contrast, embodiments of the present invention provide materials for use in medical implants that produce wear particles which exhibit benign body response properties. In some embodiments, the materials can also improve the wear resistance of the material.

BRIEF DESCRIPTION OF THE DRAWINGS

Certain preferred embodiments of medical implants in accordance with the invention, or rather a portion thereof, are described in detail below with reference to the accompanying drawings in which.

DETAILED DESCRIPTION OF THE PREFERRED EMBODIMENTS

Figure 1:
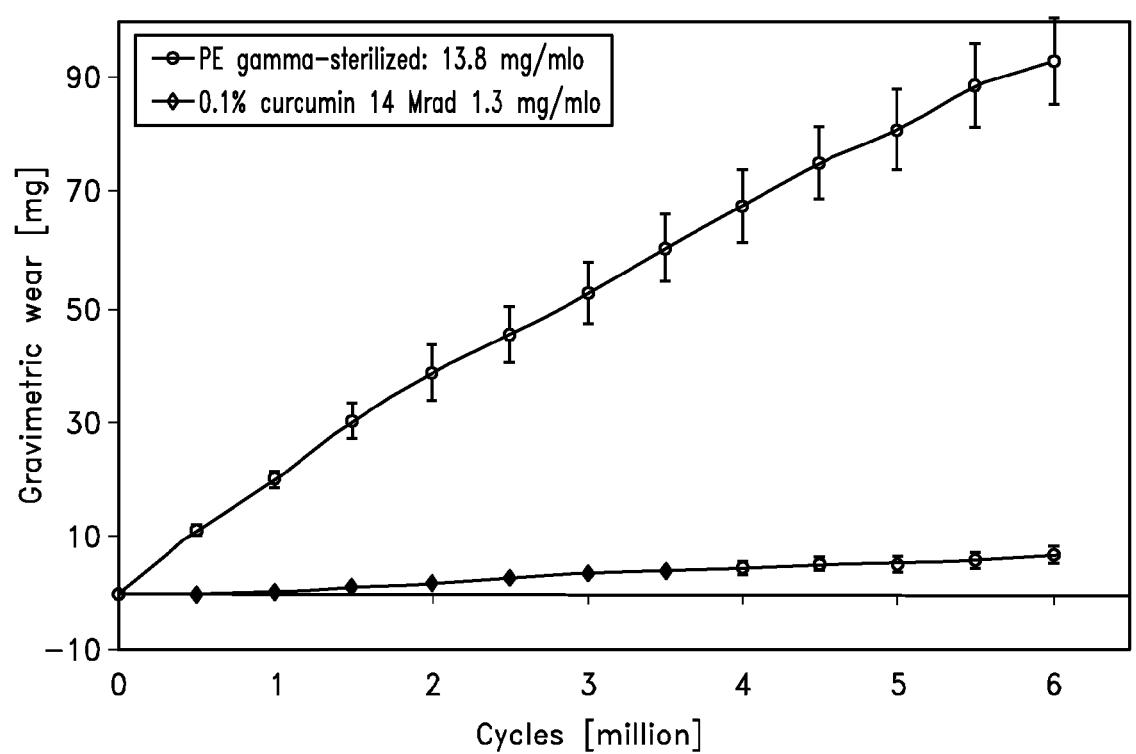
FIG. 1 depicts results from a hip simulator test.

In one embodiment, the present invention is directed to the use of one or more substances selected from the group consisting of anti-inflammatory substances, anti-microbial substances, anti-tumor substances, anti-viral substances, and/or bone stimulating substances as an additive to UHMWPE material for the production of a medical implant for imparting benign body response properties to the medical implant.

The present inventors have surprisingly found that the use of such substances as an additive to an UHMWPE material imparts considerably improved cell response properties on such a material.

In a preferred embodiment, the additive is one or more of anti-inflammatory substances in the form of curcumin, gingerol, zingerone, helenalin, salicin, salicylic acid, cannabichromene, flavonoids, in particular in the form of quercetin, resveratrol and/or myricetin, tannins, terpenes, marrubin and/or steroidal anti-inflammatory agents, in particular in the form of corticosteroids, and/or anti-microbial substances such as peptide-based substances, in particular lactoferrine, or non-peptide based substances, in particular penicilline and/or silver, and/or anti-tumor substances such as anthracyclines, curcumin and/or helenalin, and/or anti-viral substances such as tannin, and/or bone-stimulating substances such as peptide-based substances, in particular lactoferrine, and/or non-peptide based substances, in particular in the form of quercetin and/or diphosphonates, and/or growth factors, in particular of the BMP family, further in particular BMP-2.

In a particularly preferred embodiment, the additive is curcumin.

The additive is used in a wide range of amounts. A preferred embodiment is the use of the additive in an amount of from 0.0001 to 5 wt.-%, based on the total weight of the medical implant, preferably 0.001 to 1 wt. %, and even more preferably 0.02 to 0.1 wt %.

While the additives are useful in any sort of medical implants, they are of particular value in artificial joint replacements. Such artificial joint replacements produce considerable numbers of wear particles which display benign body response properties, when the additives are used.

In a further aspect, embodiments of the present invention are directed to an UHMWPE material for use in a medical implant, in particular an orthopaedic joint replacement, comprising the following characteristics:

The wear debris will have anti-inflammatory properties, such that the osteolysis cascade resulting from inflammation will be reduced.

The wear debris will have other beneficial properties, such as anti-tumor, anti-microbial (e.g. anti-bacterial), anti-viral, bone stimulating or bone resorption inhibiting properties.

The material allows an easy, facile production process. Curcumin powder or another anti-inflammatory additive is mixed with UHMWPE powder prior to sintering. Irradiation can be performed in air without using a complicating protective environment. Alternatively the material can be used without irradiation.

The addition of curcumin or the like protects the material from oxidative degradation, as demonstrated by accelerated aging studies (see Example 1).

In a further aspect, embodiments of the present invention are directed to an UHMWPE material having benign body response properties, comprising UHMWPE and one or more additives selected from the group consisting of anti-inflammatory substances, anti-microbial substances, anti-tumor substances, anti-viral substances, and/or bone stimulating substances as an additive to UHMWPE material for the production of a medical implant for imparting benign body response properties to the medical implant.

In a preferred embodiment, the additive is an anti-inflammatory substance in the form of curcumin, gingerol, zingerone, helenalin, salicin, salicylic acid, cannabichromene, flavonoids, in particular in the form of quercetin, resveratrol and/or myricetin, tannins, terpenes, marrubin and/or steroidal anti-inflammatory agents, in particular in the form of corticosteroids, and/or anti-microbial substances such as peptide-based substances, in particular lactoferrine, or non-peptide based substances, in particular penicilline and/or silver, and/or anti-tumor substances such as anthracyclines, curcumin and/or helenalin, and/or anti-viral substances such as tannin, and/or bone-stimulating substances such as peptide-based substances, in particular lactoferrine, and/or non-peptide based substances, in particular in the form of quercetin and/or diphosphonates, and/or growth factors, in particular of the BMP family, further in particular BMP-2.

In a particularly preferred embodiment, the additive is curcumin.

In a further preferred embodiment, the additive is used in the UHMWPE material described above in an amount of 0.0001 to 5 wt.-%, based on the total weight of the medical implant, preferably 0.001 to 1 wt. %, and even more preferably 0.02 to 0.1 wt %.

Embodiments of the present invention are also directed to a medical implant prepared from a preform material in the form of the UHMWPE material described above.

The term "preform" is used throughout the current specification to mean a consolidated block, sheet or rod of the UHMWPE material, and in particular one which may then be subjected to further processing and finally from which an end product in the form of a medical implant can be obtained.

The material according to the present embodiment of the invention may, but does not have to, be irradiated. Irradiation of the UHMWPE preform by gamma or electron beam radiation will lead to an increase in the crosslink density. An equivalent measure of the density of crosslinks of the material is that of the molecular weight between the crosslinks. Clearly, the higher the crosslink density between the individual UHMWPE polymers, the lower the molecular weight between the crosslinks. Preferably, the irradiation with the gamma or electron beam is at a dose of between 5 and 20 Mrad, which value can be chosen dependent upon the final properties of the UHMWPE material required. Changing the irradiation dose will lead to a difference in the molecular weight between crosslinks and is intended to be chosen on the basis of the desired final product.

A further preferred embodiment is the medical implant described above, whereby the preform material has been irradiated with gamma or electron beam irradiation at a dose of 2 and 20 Mrad, preferably 4 to 20 Mrad, more preferably 5 to 20 Mrad and particulary preferred 5 to 15 Mrad. The exact value for the irradiation dose can be chosen dependent upon the final properties of the UHMWPE material required. The irradiation can be performed in air under ambient conditions. In another aspect, the irradiation may also be performed under vacuum or in a protective environment such as nitrogen or argon gas atmosphere.

On the other hand, the preform material according to the present embodiment of the invention can also be used without being irradiated or irradiated with a very small dose of irradiation.

In another embodiment of the invention, the material is therefore not irradiated by gamma or electron beam irradiation, or irradiated by gamma or electron beam irradiation at a dose of less than 2 Mrad.

A further preferred embodiment is a medical implant, whereby the preform material has been irradiated in air.

In a further preferred embodiment, the preform material has not been annealed or further heated after irradiation.

Preferably, the medical implant according to this embodiment of the present invention is an artificial joint replacement.

In another embodiment, the present invention is directed to a medical implant as described above for the treatment of inflammatory diseases, microbial diseases, neoplastic diseases, viral diseases, and/or bone-degrading diseases. Preferably, the additive is curcumin and the medical implant is for the treatment of inflammatory diseases.

In another embodiment, the present invention is directed to a method for fabricating an UHMWPE material having benign body response properties, comprising the steps:

mixing a material comprising UHMWPE with a quantity of an additive selected from the group consisting of anti-inflammatory substances, anti-microbial substances, anti-tumor substances, anti-viral substances, and/or bone stimulating substances, moulding the mixture to create a preform by applying a temperature above the melting point of the UHMWPE.

In another embodiment of the present invention, additives selected from the group consisting of anti-inflammatory substances, anti-microbial substances, anti-tumor substances, anti-viral substances, and/or bone stimulating substances may be incorporated into a preform or a final implant by diffusion. Diffusion may be executed by directly submerging the preform or final implant into the pure additive or a solution of the additive in an appropriate solvent. The additive may also be incorporated into a preform or into a final implant by the aid of supercritical gases such as, but not limited to, supercritical carbon dioxide.

In a preferred embodiment of the method described above, the additive is one or more of anti-inflammatory substances in the form of curcumin, gingerol, zingerone, helenalin, salicin, salicylic acid, cannabichromene, flavonoids, in particular in the form of quercetin, resveratrol and/or myricetin, tannins, terpenes, marrubin and/or steroidal anti-inflammatory agents, in particular in the form of corticosteroids, and/or anti-microbial substances such as peptide-based substances, in particular lactoferrine, or non-peptide based substances, in particular penicilline and/or silver, and/or anti-tumor substances such as anthracyclines, curcumin and/or helenalin, and/or anti-viral substances such as tannin, and/or bone-stimulating substances such as peptide-based substances, in particular lactoferrine, and/or non-peptide based substances, in particular in the form of quercetin and/or diphosphonates, and/or growth factors, in particular of the BMP family, further in particular BMP-2.

The formation of the UHMWPE material according to some embodiments of the present invention typically begins with mixing the additive with the UHMWPE powder. In the examples described hereafter, the UHMWPE powder will be of Ticona GUR® 1020 medical grade UHMWPE. Such powder is well known and can be commercially obtained. Of course, also any other UHMWPE powders can be used (for example Ticona GUR® 1050, DSM UH210, Basell 1900, UHMWPE powders with a high purity). It is preferable that during the mixing process of the additive and UHMWPE powder, a fully homogeneous mixture will be obtained. Once the additive and UHMWPE powder have been mixed, they are moulded into the preform at a temperature which is above the melting point of the UHMWPE powder. At this stage, the further specification of the temperature is not especially crucial for the moulding step. Increased temperatures will lead to a more rapid moulding of the material into the preform.

Typically, the moulding of the additive material and UHMWPE powder, will be at a temperature which is above the melting point of the UHMWPE powder, but which is also preferably below the degradation temperature of the additive material. Clearly, temperature affects most compounds and indeed the same holds true for the additive material. It is preferable, although not necessary, to maintain the temperature of the moulding step below the degradation temperature of this additive material, as this leads to an improved final product. In one embodiment of the present invention, moulding of the UHMWPE powder is done in an inert atmosphere such as argon or nitrogen.

Typically, the moulding step to produce a preform is performed by compression moulding of sheets, slabs or rods. In another embodiment of the present invention, the moulding step can also be performed by direct compression moulding a final implant or a nearly final implant that only requires minor machining after moulding or other means to directly produce a final or nearly final implant. In yet another aspect, the preform may also be produced by ram extrusion of the UHMWPE powder blend.

In a preferred embodiment, the method according to the present invention comprises the further step of irradiating the preform with either gamma or electron beam radiation at a dose of 2 to 20 Mrad. The irradiation can be performed in air under ambient conditions. In another aspect, the irradiation may also be performed under vacuum or in a protective environment such as nitrogen or argon gas atmosphere.

In an alternative embodiment, the method according to the present invention comprises the further step of irradiating the preform with either gamma or electron beam radiation at a dose of less than 2 Mrad.

Preferably, no annealing or further heating is performed on the preform.

The method according to a particularly preferred embodiment of the present invention further comprises one or more of the following steps: the preform is shaped into an implant; the implant is packaged and either sterilized with a gamma irradiation at between 2 and 4 Mrad or the implant is sterilized with exposure to ethylene oxide or a gas plasma.

Obtaining the end product from a preform is done by any of the known standard methods, and most typically is accomplished by removing or machining the unwanted parts of the preform to give the final shaped product. This preform can be subjected to a stress-relief annealing process as is mentioned in the ISO 5834-2 standard.

In a further embodiment, the present invention is directed to a method for treating an inflammatory disease, a microbial infection, a neoplastic disease, a viral infection and/or a bone degrading disease in animals and humans, characterised by administering a medical implant as described above.

Looking at the Comparative Examples provided at the end of the specification, several examples of materials according to the present embodiment of the invention are shown. In these Comparative Examples, samples are shown with no additive material, or curcumin as an additive material.

Looking at the data shown in Example 1 and especially in Table 1 therein, a comparison of the free radical content, maximum oxidation index after aging (max. OI), bulk oxidation index after aging (bulk OI) and the molecular weight between crosslinks MC of samples with and without curcumin at a variety of irradiation doses are presented. As can be seen, the UHMWPE samples comprising the additive material curcumin have a free radical content and a molecular weight between crosslinks MC comparable to an UHMWPE material which has had the same dose of gamma irradiation, but which is not provided with additive material according to the present embodiment of the invention. However, there are large differences in the maximum and bulk oxidation indices after artificial aging. This artificial aging has been performed as prescribed in ASTM F 2003 in an oxygen bomb at 5 atm oxygen pressure and 70° C. for fourteen days. Immediately evident is that the UHMWPE sample containing curcumin is significantly lower in maximum and a bulk oxidation index after aging when compared to UHMWPE samples not containing curcumin. Such an increased oxidation index is undesirable, as it means that the UHMWPE preform will oxidize more readily during storage or in use as an implant, which will lead to an embrittlement of the material and significant complications such as increased wear or failure of the implant.

Numerous mechanical properties of the materials are shown in Example 2 and in Table 2 presented therein. As can be seen from this Table, the yield stress, tensile strength, elongation at break and charpy impact strength of the materials according to the present embodiment of the invention are compared with a standard material which possesses no additive.

This example and results therein clearly show that the addition of the additive material in such quantities does not have any significant detrimental effect to the final mechanical properties of the UHMWPE material with an additive. Not only, therefore, do the materials according to the present embodiment of the invention show an improvement in oxidation characteristics as compared with a material not comprising the additive, but the provision of the additive does not significantly affect the final mechanical properties. Again, this is of significant advantage when the material is to be used as an implant, as it shows that the material has maintained its integrity, and is still of use as an implant.

According to Example 3, the hip simulator testing of two materials was performed against 28 mm ceramic balls on an AMTI hip simulator reproducing the human gait cycle with a frequency of 1.2 Hz and newborn calf serum (30 g/l protein concentration) as lubricant. Gravimetric wear was determined by weighing the acetabular cups every 0.5 mio cycles and by correcting the obtained results with a soak control cup.

The two samples were an UHMWPE material comprising 0.1 wt.-% curcumin, irradiated with 14 Mrad (sample according to the present embodiment of the invention) and a gamma-sterilized PE sample (comparative). As can be seen from the data provided in FIG. 1, the UHMWPE material according to this embodiment of the present invention shows much lower gravimetric wear when compared with the comparative gamma-sterilized PE material in the hip simulator.

According to the results of all performed experiments, the following characteristics for an UHMWPE material whose wear debris will have anti-inflammatory response can be nominated:

The material according to the present invention can be a mixture of UHMWPE resin powder with one or more anti-inflammatory agents.

The anti-inflammatory agent can be, but is no limited to, curcumin.

The anti-inflammatory agent can be mixed with UHMWPE powder prior to sintering a preform.

Orthopaedic implant bearing components made from material according to embodiments of the present invention can generate wear debris with anti-inflammatory properties, such that the osteolysis cascade resulting from inflammation will be reduced.

An advantage of embodiments of the present invention compared to the prior art include the release of wear particles comprising benign body response properties, in particular anti-inflammatory properties, released by an orthopaedic implant. Up to now, a reduction of osteolysis was primarily achieved by reducing the number of wear particles with the use of highly crosslinked UHMWPE.

The present embodiment of the invention describes a reduction of osteolytic bone resorption primarily through anti-inflammatory wear particles. In addition, the number of wear particles may, but does not have to, be reduced by crosslinking the UHMWPE by means of gamma or e-beam radiation.

Therefore, the osteolysis cascade resulting from inflammation will not only be reduced by the reduced number of particles but also by the anti-inflammatory properties of the particles themselves.

COMPARATIVE EXAMPLES

Gamma-sterilized UHNIWPE was compression moulded into sheets (GUR® 1020, Quadrant, Germany), machined, packaged in inert gas atmosphere and gamma sterilized with a dose of 3 Mrad. Curcumin blended samples were produced by mixing UHMWPE resin powder with 0.03 to 0.1 wt.-% curcumin, compression moulded into blocks, gamma-irradiated with 7 to 14 Mrad in air and machined into the desired shape. No thermal post-irradiation treatment was applied. The following tests were performed with these materials:

EXAMPLES

Example 1

Free radical content, oxidation indices and molecular weight between crosslinks.

TABLE 1

| | Free Radical Content [$g^{-1}$] | Max. OI after aging [—] | Bulk OI after aging [—] | $M_c$ [g/mol] |
|---|---|---|---|---|
| PE gamma-sterilized | 1.46E+18 | 0.24 | 0.20 | 6980 |
| PE 7 Mrad | 3.03E+18 | 0.35 | 0.33 | 5430 |
| PE 14 Mrad | 5.87E+18 | 0.55 | 0.50 | 3520 |
| 0.1% curcumin 7 Mrad | 3.19E+18 | 0.08 | <0.05 | 5770 |
| 0.1% curcumin 14 Mrad | 6.27E+18 | 0.11 | <0.05 | 3970 |
| 0.1% curcumin 20 Mrad | 1.44E+19 | 0.14 | 0.09 | |
| 0.05% curcumin 10 Mrad | 8.77E+18 | 0.07 | 0.06 | |
| 0.05% curcumin 14 Mrad | 1.19E+19 | 0.13 | 0.07 | |
| 0.03% curcumin 10 Mrad | 8.33E+18 | 0.07 | 0.05 | |
| 0.03% curcumin 14 Mrad | 1.13E+19 | 0.10 | 0.07 | |

Oxidation indices (OI) were quantified by Fourier Transform Infrared Spectroscopy (FTIR) according to ASTM F2102-06. Oxidation profiles were recorded with 150 µm thick slices to a depth of 2.5 mm from the surface. Prior to the OI measurements, all samples were artificially aged in an oxygen bomb at 5 bar oxygen pressure and 70° C. for two weeks (ASTM F2003-02).

Crosslink density, represented by the molecular weight between crosslinks (MC), was obtained by swelling experiments according to ASTM D 2767-95 Method C on 3 samples per material (10×10×10 mm).

Example 2

Mechanical Properties

TABLE 2

| | Yield Stress [MPa] | Tensile Strength [MPa] | Elongation at Break [%] | Charpy Impact Strength [kJ/m$^2$] |
|---|---|---|---|---|
| PE gamma-sterilized | 25.8 ± 1.1 | 49.6 ± 6.5 | 414.0 ± 42.0 | 152.2 ± 6.9 |
| PE 7 Mrad remelted | 22.6 ± 0.6 | 32.2 ± 3.6 | 351.3 ± 25.9 | 96.9 ± 1.0 |
| PE 7 Mrad | 23.8 ± 0.6 | 43.7 ± 1.9 | 367.7 ± 15.9 | 108.7 ± 1.1 |
| PE 14 Mrad | 25.8 ± 0.4 | 39.5 ± 9.3 | 241.1 ± 64.6 | 68.8 ± 0.8 |
| 0.1% curcumin 7 Mrad | 23.2 ± 0.4 | 39.9 ± 2.6 | 378.0 ± 12.9 | 131.0 ± 3.6 |
| 0.1% curcumin 14 Mrad | 26.0 ± 0.5 | 40.2 ± 3.3 | 277.3 ± 18.2 | 65.5 ± 2.2 |
| 0.1% curcumin 20 Mrad | 27.3 ± 0.5 | 43.3 ± 1.3 | 231.4 ± 9.0 | 44.5 ± 1.0 |
| 0.05% curcumin 10 Mrad | 26.4 ± 0.5 | 44.9 ± 1.9 | 311.1 ± 14.2 | 68.5 ± 1.9 |
| 0.05% curcumin 14 Mrad | 26.8 ± 0.4 | 45.4 ± 3.1 | 273.9 ± 19.4 | 56.8 ± 1.2 |
| 0.03% curcumin 10 Mrad | 26.6 ± 0.2 | 49.6 ± 1.2 | 335.5 ± 9.1 | 66.6 ± 0.9 |
| 0.03% curcumin 14 Mrad | 26.8 ± 0.6 | 45.7 ± 4.6 | 271.0 ± 29.8 | 53.3 ± 0.4 |

Mechanical testing: Double-notched Charpy impact testing was performed according to DIN EN ISO 11542-2 (min. 4 specimens per material) and tensile testing according to ASTM D638 (min. 5 specimens per material) using a test speed of 50 mm/min.

Example 3

Hip Simulator Data

Hip simulator testing against 28 mm ceramic balls was performed on an AMTI hip simulator reproducing the human gait cycle with a frequency of 1.2 Hz and newborn calf serum (30 g/l protein concentration) as lubricant. Gravimetric wear was determined by weighing the acetabular cups every 0.5 mio cycles and by correcting the obtained results with a soak control cup.

The result of the hip simulator testing is shown in FIG. 1.

Example 4

Anti-Inflammatory Response

Curcumin blended samples were produced by mixing UHMWPE resin powder with 1 wt.-% curcumin, compression moulded into blocks, gamma-irradiated with 14 Mrad in air and machined into the desired shape. No thermal post-irradiation treatment was applied. A standard, conventional highly crosslinked/remelted material was used as control.

The anti-inflammatory effect of 1% curcumin impregnated polyethylene discs on LPS stimulated PMA differentiated U937 cells was assessed. U937 human monocyte-like cells were cultured and expanded in their appropriate culture media. Cells were seeded at in 24 well inserts in 200 µl of culture media containing 20 nM of PMA, an additional 1 ml of the same PMA containing culture media was added to each well outside of the inserts. Plates were then incubated for 24 hours at 37° C. and 5% CO2 to differentiate into macrophage-like cells. After 24 hours incubation with PMA, media was removed from the cells and replaced with 200 µl of culture media and the inserts were transferred to fresh 24 well plates containing 1 ml of media (without PMA). The cells were then returned to incubate at 37° C. and 5% CO2 for a further 72 hours. After 72 hours the inserts were transferred to fresh 24 well plates containing the sample materials (inserts were sat on top of the sample materials) and 500 µl of media. At this point, media was also removed from inside the inserts and replaced with 200 µl of fresh media. The plates were then incubated for a further 24 hours at 37° C. prior to addition of LPS. After 24 hours 0 ng/ml, 1 ng/ml or 20 ng/ml of LPS was then added to the cells by replacing the media (inside and outside the inserts) with media containing the appropriate amount of LPS (200 µl inside the inserts and 500 µl outside the inserts). The plates were then returned to incubate at 37° C. for 8 hours. At the appropriate incubation period, media from inside the inserts was carefully removed and stored at −70° C. for subsequent cytokine assessment.

Once media had been collected, the conditioned media was defrosted at room temperature. The conditioned media was then assessed by ELISA kits specific for TNF-α following the manufacturers instructions. In brief; ELISA plates were coated overnight with the appropriate capture antibody. The plates were then washed 3 times with wash buffer and blocked with assay diluent for 1 hour at room temperature. After blocking the plates were washed 3 times in wash buffer and 100 µl of each sample solution was added to the wells to incubate at room temperature for 2 hours. After 2 hours incubation the plates were washed 5 times in wash buffer and incubation with the specific primary antibody (together with the enzyme concentrate for the TNF) for 1 hour at room temperature the plates were then washed. After thorough washing the plates were then incubated at room temperature in the dark with the substrate solution for 30 minutes. After 30 minutes stop solution was then added to each well and the plates were read at 450 nm and 570 nm after shaking for 1 minute.

Figure 2:
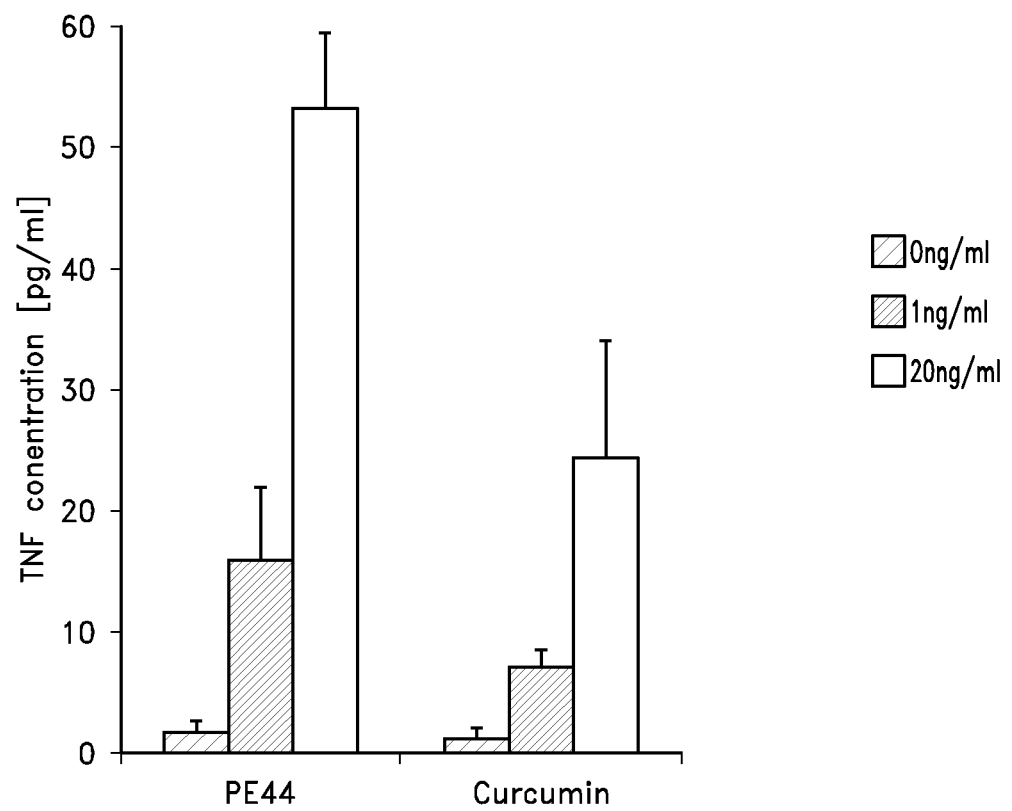
FIG. 2 depicts results indicating an anti-inflammatory effect.

Results: TNF secreted from U937 cells (macrophage-like cells) following 8 hours incubation with 0, 1 or 20 ng/ml of LPS is shown in FIG. 2.

Curcumin blended UHMWPE reduced TNF secretion from macrophage-like cells (U937) after 8 hours incubation with LPS when compared to the standard highly crosslinked/remelted UHMWPE (PE44), thus showing some anti-inflammatory effect.

What is claimed is:
1. A method for fabricating an UHMWPE material having benign body response properties comprising the steps:
   mixing a material comprising UHMWPE with a quantity of one or more additives selected from the group consisting of anti-inflammatory substances, anti-microbial substances, anti-tumor substances, anti-viral substances, and/or bone stimulating substances; and
   moulding the mixture to create a preform by applying a temperature above the melting point of the UHMWPE but below the degradation temperature of the one or more additives, and optionally forming a medical implant from the preform.

2. The method according to claim 1, whereby the additive is one or more of:
- anti-inflammatory substances in the form of curcumin, gingerol, zingerone, helenalin, salicin, salicylic acid, cannabichromene, flavonoids, in particular in the form of quercetin, resveratrol and/or myricetin, tannins, terpenes, marrubin or steroidal anti-inflammatory agents, in particular in the form of corticosteroids; and/or
- anti-microbial substances such as peptide-based substances, in particular lactoferrine, or non-peptide based substances, in particular penicillin and/or silver; and/or
- anti-tumor substances such as anthracyclines, curcumin and/or helenalin; and/or
- anti-viral substances such as tannin; and/or
- bone-stimulating substances such as peptide-based substances, in particular lactoferrine, and/or non-peptide based substances, in particular in the form of quercetin and/or diphosphonates, and/or growth factors, in particular of the BMP family.

3. The method according to claim 1, further comprising the step of irradiating the preform with either gamma or electron beam radiation at a dose of about 2 Mrad to about 20 Mrad.

4. The method according to claim 1, further comprising the step of irradiating the preform with either gamma or electron beam radiation at a dose of less than about 2 Mrad.

5. The method according to claim 1, whereby no annealing or further heating is performed on the preform.

6. The method according to claim 1, further comprising the following steps:
- shaping the preform into an implant;
- packaging the implant and either sterilizing the implant with a gamma irradiation at between about 2 Mrad and about 4 Mrad or sterilizing the implant with exposure to ethylene oxide or a gas plasma.

7. The method according to claim 1, further comprising:
- forming a medical implant from the preform; and
- administering the medical implant for treating an inflammatory disease, a microbial infection, a neoplastic disease, a viral infection and/or a bone degrading disease in animals and humans.

8. The method according to claim 1, whereby the additive is in an amount of 0.0001 to 5 wt. %, based on the total weight of the medical implant.

9. The method according to claim 1, further comprising the step of irradiating the preform in air.

10. The method according to claim 3, whereby no annealing or further heating is performed on the preform after the irradiating.

11. The method according to claim 7, whereby the medical implant is an artificial joint replacement.

12. The method according to claim 1, further comprising the step of using the preform for treating inflammatory diseases.

13. The method according to claim 8, whereby the additive is in an amount of 0.001 to 1 wt. %, based on the total weight of the medical implant.

14. The method according to claim 13, whereby the additive is in an amount of 0.02 to 0.1 wt. %, based on the total weight of the medical implant.

15. The method according to claim 1, further comprising the step of irradiating the preform with either gamma or electron beam radiation.

16. The method according to claim 15, whereby the irradiating is at a dose of up to about 20 Mrad.

17. The method according to claim 16, whereby the irradiating is at a dose of about 4 Mrad to about 20 Mrad.

18. The method according to claim 17, whereby the irradiating is at a dose of about 5 Mrad to about 20 Mrad.

19. The method according to claim 15, whereby no annealing or further heating is performed on the preform after the irradiating.

20. The method according to claim 1, further comprising the following steps:
- shaping the preform into a medical implant; and
- irradiating the medical implant with either gamma or electron beam radiation.

21. A method for fabricating an UHMWPE material having benign body response properties comprising the steps:
- providing a material comprising UHMWPE and moulding it to create a preform by applying a temperature above the melting point of the UHMWPE; and
- incorporating an additive into the preform by diffusion with the aid of a supercritical gas;
- wherein the applying of the temperature above the melting point of the UHMWPE is below the degradation temperature of the additive.

22. The method according to claim 21, wherein the additive is selected from the group consisting of anti-inflammatory substances, anti-microbial substances, anti-tumor substances, anti-viral substances, and/or bone stimulating substances.

23. The method according to claim 21, wherein the supercritical gas comprises supercritical carbon dioxide.

24. A method for fabricating a medical implant having benign body response properties comprising the steps:
- providing a material comprising UHMWPE and moulding it to create a preform by applying a temperature above the melting point of the UHMWPE;
- forming a medical implant from the preform; and
- incorporating an additive into the medical implant by diffusion with the aid of a supercritical gas;
- wherein the applying of the temperature above the melting point of the UHMWPE is below the degradation temperature of the additive.

25. The method according to claim 24, wherein the additive is selected from the group consisting of anti-inflammatory substances, anti-microbial substances, anti-tumor substances, anti-viral substances, and/or bone stimulating substances.

26. The method according to claim 24, wherein the supercritical gas comprises supercritical carbon dioxide.

27. The method according to claim 1, wherein the one or more additives comprises curcumin.

28. The method according to claim 21, wherein the additive is curcumin.

29. The method according to claim 24, wherein the additive is curcumin.

* * * * *